United States Patent
Rezai

(10) Patent No.: US 8,229,564 B2
(45) Date of Patent: Jul. 24, 2012

(54) NEUROMODULATORY METHODS FOR TREATING PULMONARY DISORDERS

(75) Inventor: Ali R. Rezai, Shaker Heights, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 13/196,636

(22) Filed: Aug. 2, 2011

(65) Prior Publication Data

US 2011/0301664 A1 Dec. 8, 2011

Related U.S. Application Data

(63) Continuation of application No. 12/333,162, filed on Dec. 11, 2008, now Pat. No. 8,155,744.

(60) Provisional application No. 61/013,378, filed on Dec. 13, 2007.

(51) Int. Cl.
 *A61N 1/36* (2006.01)
(52) U.S. Cl. .......................................... 607/42
(58) Field of Classification Search .................. 607/2, 9, 607/42
See application file for complete search history.

(56) References Cited

U.S. PATENT DOCUMENTS

| | | | |
|---|---|---|---|
| 5,531,779 A | 7/1996 | Dahl et al. | |
| 6,411,852 B1 | 6/2002 | Danek et al. | |
| 6,445,953 B1 | 9/2002 | Bulkes et al. | |
| 6,572,543 B1 | 6/2003 | Christopherson et al. | |
| 6,610,713 B2 | 8/2003 | Tracey | |
| 6,633,779 B1 | 10/2003 | Schuler et al. | |
| 6,748,275 B2 | 6/2004 | Lattner et al. | |
| 6,907,285 B2 | 6/2005 | Denker et al. | |
| 7,277,757 B2 | 10/2007 | Casavant et al. | |
| 7,747,324 B2 | 6/2010 | Errico et al. | |
| 2003/0093128 A1 | 5/2003 | Freed et al. | |
| 2003/0100924 A1 | 5/2003 | Foreman et al. | |
| 2003/0181951 A1 | 9/2003 | Cates | |

(Continued)

FOREIGN PATENT DOCUMENTS

RU 2 108 817 C1 4/1998

(Continued)

OTHER PUBLICATIONS

Gromova et al., "Sinusoidal Modulated Currents in Comprehensive Treatment of Children with Bronchial Asthma", *Voprosy kurortologii fizioterapii,I lechebnoi fizicheskol kultury*, May-Jun; (3):45-7 (1981).

(Continued)

*Primary Examiner* — Scott Getzow
*Assistant Examiner* — Amanda Patton
(74) *Attorney, Agent, or Firm* — Tarolli, Sundheim, Covell & Tummino LLP

(57) ABSTRACT

A method for treating asthma in a subject includes inserting a therapy delivery device into a vessel of a subject. The therapy delivery device is advanced to a point substantially adjacent an intraluminal target site of the autonomic nervous system. Next, the therapy delivery device is activated to deliver a therapy signal to the intraluminal target site to treat the asthma. The intraluminal target site is in electrical communication with nervous tissue selected from the group consisting of a spinal nerve, pre- or post-ganglionic autonomic fibers, a sympathetic chain ganglion, a thoracic sympathetic chain ganglion, a cervical ganglion, a lower cervical ganglion, an inferior cervical ganglion, an intramural ganglion, a splanchnic nerve, an esophageal plexus, a cardiac plexus, a pulmonary plexus, an anterior pulmonary plexus, a posterior pulmonary plexus, a celiac plexus, a hypogastric plexus, an inferior mesenteric ganglion, a celiac ganglion, and a superior mesenteric ganglion.

13 Claims, 9 Drawing Sheets

U.S. PATENT DOCUMENTS

| | | |
|---|---|---|
| 2003/0181958 A1 | 9/2003 | Dobak, III |
| 2003/0181959 A1 | 9/2003 | Dobak, III |
| 2004/0030362 A1 | 2/2004 | Hill et al. |
| 2004/0153127 A1 | 8/2004 | Gordon et al. |
| 2004/0230251 A1 | 11/2004 | Schuler et al. |
| 2004/0243182 A1 | 12/2004 | Cohen et al. |
| 2004/0249416 A1 | 12/2004 | Yun et al. |
| 2005/0021092 A1 | 1/2005 | Yun et al. |
| 2005/0021102 A1 | 1/2005 | Ignagni et al. |
| 2005/0137645 A1 | 6/2005 | Voipio et al. |
| 2005/0288728 A1 | 12/2005 | Libbus et al. |
| 2005/0288729 A1 | 12/2005 | Libbus et al. |
| 2006/0058852 A1 | 3/2006 | Koh et al. |
| 2006/0155344 A1 | 7/2006 | Rezai et al. |
| 2006/0224211 A1 | 10/2006 | Durand et al. |
| 2006/0229677 A1 | 10/2006 | Moffitt et al. |
| 2006/0247729 A1 | 11/2006 | Tehrani et al. |
| 2006/0259084 A1 | 11/2006 | Zhang et al. |
| 2006/0282127 A1 | 12/2006 | Zealear |
| 2006/0282131 A1 | 12/2006 | Caparso et al. |
| 2006/0282145 A1 | 12/2006 | Caparso et al. |
| 2006/0293720 A1 | 12/2006 | DiLorenzo |
| 2007/0021795 A1 | 1/2007 | Tehrani |
| 2007/0027496 A1 | 2/2007 | Parnis et al. |
| 2007/0106338 A1 | 5/2007 | Errico |
| 2007/0106339 A1 | 5/2007 | Errico et al. |
| 2007/0118183 A1 | 5/2007 | Gelfand et al. |
| 2007/0150009 A1 | 6/2007 | Kveen et al. |
| 2007/0156198 A1 | 7/2007 | Rossing et al. |
| 2007/0156199 A1 | 7/2007 | Koh et al. |
| 2007/0173893 A1 | 7/2007 | Pitts |
| 2007/0213782 A1 | 9/2007 | Shaw |
| 2007/0255379 A1 | 11/2007 | Williams et al. |
| 2008/0039904 A1 | 2/2008 | Bulkes et al. |

FOREIGN PATENT DOCUMENTS

| | | |
|---|---|---|
| WO | WO-93/01862 A1 | 2/1993 |

OTHER PUBLICATIONS

Karashurov et I., "Radio Frequency Electrostimulation of the Gangliated Cord of the Sympathetic Nerve in Patients with Bronchial Asthma", *Surgery* (*Khigurgiia*), 2000, 1:44-46.

Gudovsky et al., "Surgical Treatment of Bronchial Asthma", *Surgery* (*Khigurgiia*), 2002, 7:14-18.

Karashurov et al., "Evolution of Surgical Treatment of Bronchial Asthma", *Surgery* (*Khigurgiia*), 1999, 11:57-60.

NEUROMODULATORY METHODS FOR TREATING PULMONARY DISORDERS

RELATED APPLICATIONS

This application is a continuation of U.S. patent application Ser. No. 12/333,162, filed Dec. 11, 2008, now U.S. Pat. No. 8,155,744 which claims priority from U.S. Provisional Application No. 61/013,378, filed Dec. 13, 2007, U.S. patent application Ser. No. 11/121,006, filed May 4, 2005, and U.S. patent application Ser. No. 11/222,766, filed Sep. 12, 2005. The subject matter of the aforementioned applications is incorporated herein by reference in their entireties.

TECHNICAL FIELD

The present invention relates generally to neuromodulatory methods, and more particularly to transvascular neuromodulatory methods for treating pulmonary disorders.

BACKGROUND OF THE INVENTION

Diseases and disorders of the pulmonary system are among the leading causes of acute and chronic illness in the world. Pulmonary diseases or disorders may be organized into various categories, including, for example, breathing rhythm disorders, obstructive diseases, restrictive diseases, infectious diseases, pulmonary vasculature disorders, pleural cavity disorders, and others. Pulmonary dysfunction may involve symptoms such as apnea, dyspnea, changes in blood or respiratory gases, symptomatic respiratory sounds, e.g., coughing, wheezing, respiratory insufficiency, and/or general degradation of pulmonary function, among other symptoms.

A variety of methods are currently used to treat pulmonary diseases and disorders including, for example, the use of pharmacological compositions, such as albuterol, and surgical methods such as lung volume reduction surgery. Another method used to treat pulmonary disease and disorders involves electrostimulation of various nerves, such as the vagus and phrenic nerves, to modulate pulmonary function. Such electrostimulatory methods, however, are often highly invasive and offer only short-term symptomatic relief.

SUMMARY OF THE INVENTION

According to one aspect of the present invention, a method for treating a pulmonary disorder in a subject comprises the steps of inserting a therapy delivery device into a vessel of the subject, advancing the therapy delivery device to a point substantially adjacent an intraluminal target site of the autonomic nervous system (ANS), and activating the therapy delivery device to delivery a therapy signal to the intraluminal target site of the ANS to treat the pulmonary disorder. The intraluminal target site is in electrical communication with nervous tissue selected from the group consisting of a spinal nerve, a postganglionic fiber of a spinal nerve, a sympathetic chain ganglion, a thoracic sympathetic chain ganglion, a cervical ganglion, a lower cervical ganglion, an inferior cervical ganglion, an intramural ganglion, a splanchnic nerve, an esophageal plexus, a cardiac plexus, a pulmonary plexus, an anterior pulmonary plexus, a posterior pulmonary plexus, a celiac plexus, a hypogastric plexus, an inferior mesenteric ganglion, a celiac ganglion, and a superior mesenteric ganglion.

According to another aspect of the present invention, a method for treating a pulmonary disorder in a subject comprises the steps of inserting a therapy delivery device into a vessel of the subject, advancing the therapy delivery device to a point substantially adjacent an intraluminal target site of the ANS; and activating the therapy delivery device to delivery a therapy signal to the intraluminal target site of the ANS to treat the pulmonary disorder. The pulmonary disorder is selected from the group consisting of asthma, chronic obstructive pulmonary disease, cystic fibrosis, bronchiolitis, pneumonia, pulmonary thromboembolism, bronchitis, emphysema, adult respiratory distress syndrome, allergies, brochiectasis, bronchopulmonary displasia, *Chlamydia pneumonia*, chronic bronchitis, chronic lower respiratory diseases, croup, familial emphysema, high altitude pulmonary edema, idiopathic pulmonary fibrosis, interstitial lung disease, lymphangioleiomyomatosis, neonatal respiratory distress syndrome, parainfluenza, pleural effusion, pleurisy, pneumothorax, primary pulmonary hypertension, psittacosis, pulmonary edema, pulmonary embolism, pulmonary hypertension, Q fever, respiratory failure, respiratory syncytial virus, sarcoidosis, SARS, smoking, stridor, tuberculosis, and acute respiratory distress syndrome.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION

Figure 1:
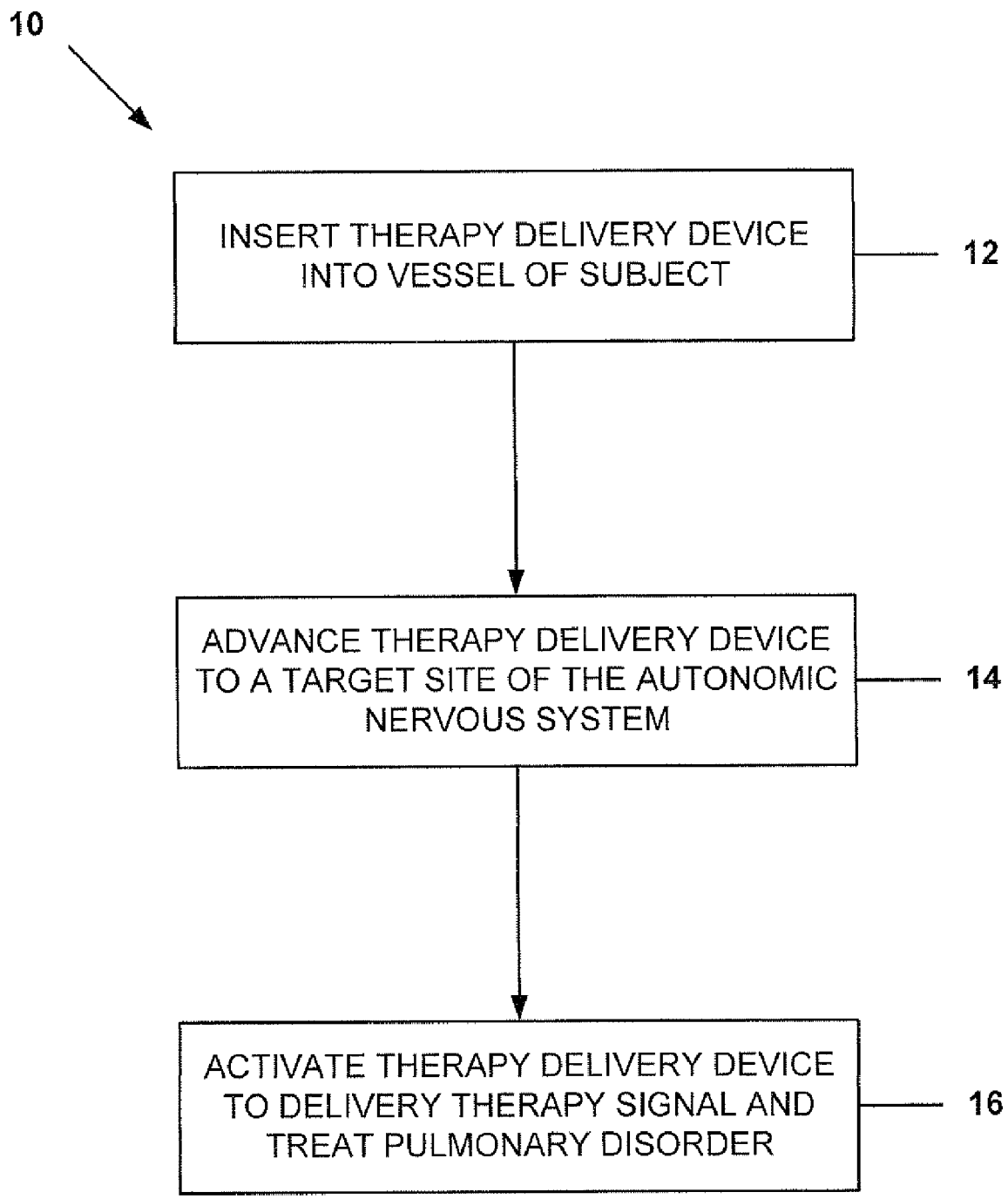
FIG. 1 is a flow diagram illustrating a method for treating a pulmonary disorder in a subject according to the present invention.

The present invention relates generally to neuromodulatory methods, and more particularly to transvascular neuromodulatory methods for treating pulmonary disorders. As representative of the present invention, FIG. 1 illustrates a method for treating a pulmonary disorder in a subject. Unless otherwise defined, all technical terms used herein have the same meaning as commonly understood by one of ordinary skill in the art to which the present invention pertains.

In the context of the present invention, the term "nervous tissue" refers to any tissues of the autonomic nervous system (ANS) including, but not limited to, neurons, axons, fibers, tracts, nerves, plexus, afferent plexus fibers, efferent plexus fibers, ganglion, pre-ganglionic fibers, post-ganglionic fibers, cervical sympathetic ganglia/ganglion, thoracic sympathetic ganglia/ganglion, afferents, efferents, and combinations thereof.

As used herein, the teims "modulate" or "modulating" refer to causing a change in neuronal activity, chemistry, and/or metabolism. The change can refer to an increase, decrease, or even a change in a pattern of neuronal activity. The terms may refer to either excitatory or inhibitory stimulation, or a combination thereof, and may be at least electrical, magnetic, optical or chemical, or a combination of two or more of these. The terms "modulate" or "modulating" can also be used to refer to a masking, altering, overriding, or restoring of neuronal activity.

As used herein, the term "pulmonary disorder" refers to both infection- and non-infection-induced disease and dysfunction of the respiratory system. Non-limiting examples of pulmonary disorders include asthma, chronic obstructive pulmonary disease, cystic fibrosis, bronchiolitis, pneumonia, pulmonary thromboembolism, bronchitis, emphysema, adult respiratory distress syndrome, allergies, brochiectasis, bronchopulmonary displasia, *Chlamydia pneumonia*, chronic bronchitis, chronic lower respiratory diseases, croup, familial emphysema, high altitude pulmonary edema, idiopathic pulmonary fibrosis, interstitial lung disease, lymphangioleiomyomatosis, neonatal respiratory distress syndrome, parainfluenza, pleural effusion, pleurisy, pneumothorax, primary pulmonary hypertension, psittacosis, pulmonary edema, pulmonary embolism, pulmonary hypertension, Q fever, respiratory failure, respiratory syncytial virus, sarcoidosis, SARS, smoking, stridor, tuberculosis, acute respiratory distress syndrome, and combinations thereof.

As used herein, the term "intraluminal target site" refers to a desired anatomical location at which a therapy delivery device may be positioned. The intraluminal target site can comprise a variety of anatomical locations, including intraluminal and extraluminal locations innervated by or in electrical communication with nervous tissue of the ANS. For example, the intraluminal target site can comprise an intravascular location in electrical communication with at least one nerve of the ANS. Intraluminal target sites contemplated by the present invention are described in further detail below.

As used herein, the term "electrical communication" refers to the ability of an electric field generated by an electrode or electrode array to be transferred, or to have a neuromodulatory effect, within and/or on at least one nerve, neuron, and/or nervous tissue of the ANS.

As used herein, the term "subject" refers to any warm-blooded organism including, but not limited to, human beings, pigs, rats, mice, dogs, goats, sheep, horses, monkeys, apes, rabbits, cattle, etc.

As used herein, the term "treating" refers to therapeutically regulating, preventing, improving, alleviating the symptoms of, and/or reducing the effects of a pulmonary disorder.

A brief discussion of the neurophysiology is provided to assist the reader with understanding the present invention. The nervous system is divided into the somatic nervous system and the ANS. In general, the somatic nervous system controls organs under voluntary control (e.g., skeletal muscles) and the ANS controls individual organ function and homeostasis. For the most part, the ANS is not subject to voluntary control. The ANS is also commonly referred to as the visceral or automatic system.

The ANS can be viewed as a "real-time" regulator of physiological functions which extracts features from the environment and, based on that information, allocates an organism's internal resources to perform physiological functions for the benefit of the organism, e.g., responds to environment conditions in a manner that is advantageous to the organism.

The ANS conveys sensory impulses to and from the central nervous system to various structures of the body such as organs and blood vessels, in addition to conveying sensory impulses through reflex arcs. For example, the ANS controls constriction and dilatation of blood vessels; heart rate; the force of contraction of the heart; contraction and relaxation of smooth muscle in various organs; lungs; stomach; colon; bladder; visual accommodation, secretions from exocrine and endocrine glands, etc. The ANS does this through a series of nerve fibers, and more specifically through efferent and afferent nerves. The ANS acts through a balance of its two components: the sympathetic nervous system (SNS) and the parasympathetic nervous system (PNS), which are two anatomically and functionally distinct systems. Both of these systems include myelinated preganglionic fibers which make synaptic connections with unmyelinated postganglionic fibers, and it is these fibers which then innervate the effector structure. These synapses usually occur in clusters called ganglia. Most organs are innervated by fibers from both divisions of the ANS, and the influence is usually opposing (e.g., the vagus nerve slows the heart, while the sympathetic nerves increase its rate and contractility), although it may be parallel (e.g., as in the case of the salivary glands). Each of these is briefly reviewed below.

The PNS is the part of the ANS controlling a variety of autonomic functions including, but not limited to, involuntary muscular movement of blood vessels and gut and glandular secretions from eye, salivary glands, bladder, rectum and genital organs. The vagus nerve is part of the PNS. Parasympathetic nerve fibers are contained within the last five cranial nerves and the last three spinal nerves and terminate at parasympathetic ganglia near or in the organ they supply. The actions of the PNS are broadly antagonistic to those of the SNS; lowering blood pressure, slowing heartbeat, stimulating the process of digestion etc. The chief neurotransmitter in the PNS is acetylcholine. Neurons of the parasympathetic nervous system emerge from the brainstem as part of the Cranial nerves III, VII, IX and X (vagus nerve) and also from the sacral region of the spinal cord via Sacral nerves. Because of these origins, the PNS is often referred to as the "craniosacral outflow".

In the PNS, both pre- and post-ganglionic neurons are cholinergic (i.e., they utilize the neurotransmitter acetylcholine). Unlike adrenaline and noradrenaline, which the body takes around 90 minutes to metabolize, acetylcholine is rapidly broken down after release by the enzyme cholinesterase. As a result the effects are relatively brief in comparison to the SNS.

Each pre-ganglionic parasympathetic neuron synapses with just a few post-ganglionic neurons, which are located near, or in, the effector organ, a muscle or gland. As noted above, the primary neurotransmitter in the PNS is acetylcholine such that acetylcholine is the neurotransmitter at all the pre- and many of the post-ganglionic neurons of the PNS. Some of the post-ganglionic neurons, however, release nitric oxide as their neurotransmitter.

The SNS is the part of the ANS comprising nerve fibers that leave the spinal cord in the thoracic and lumbar regions and supply viscera and blood vessels by way of a chain of sympathetic ganglia running on each side of the spinal column which communicate with the central nervous system via a branch to a corresponding spinal nerve. The SNS controls a variety of autonomic functions including, but not limited to, control of movement and secretions from viscera and monitoring their physiological state, stimulation of the sympathetic system inducing, e.g., the contraction of gut sphincters, heart muscle and the muscle of artery walls, and the relaxation of gut smooth muscle and the circular muscles of the iris. The chief neurotransmitter in the SNS is adrenaline, which is liberated in the heart, visceral muscle, glands and internal vessels, with acetylcholine acting as a neurotransmitter at ganglionic synapses and at sympathetic terminals in skin and skeletal muscles. The actions of the SNS tend to be antagonistic to those of the PNS.

The neurotransmitter released by the post-ganglionic neurons is nonadrenaline (also called norepinephrine). The action of noradrenaline on a particular structure, such as a gland or muscle, is excitatory in some cases and inhibitory in others. At excitatory terminals, ATP may be released along with noradrenaline. Activation of the SNS may be characterized as general because a single pre-ganglionic neuron usually synapses with many post-ganglionic neurons, and the release of adrenaline from the adrenal medulla into the blood ensures that all the cells of the body will be exposed to sympathetic stimulation even if no post-ganglionic neurons reach them directly.

Figure 2:
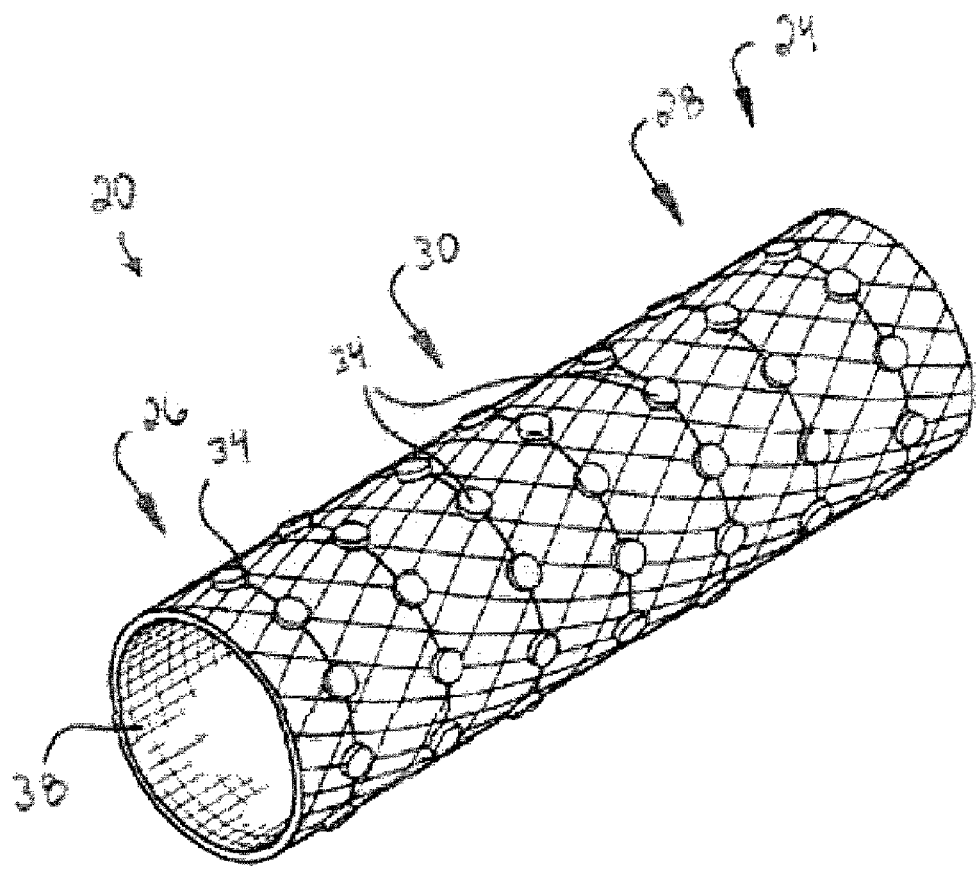
FIG. 2 is a perspective view showing a therapy delivery device for treating a pulmonary disorder.

Referring to FIG. 1, one embodiment of the present invention includes a method 10 for treating a pulmonary disorder in a subject. At 12, one step of the method 10 includes inserting a therapy delivery device 20 (FIG. 2) into a vessel 22 (FIG. 3) of a subject. One example of a therapy delivery device 20 includes an expandable electrode 24 (FIG. 2). The expandable electrode 24 can be constructed in a similar or identical manner as the device disclosed in U.S. patent Ser. No. 11/641,331, the entire contents of which are hereby incorporated by reference. It will be appreciated that the therapy delivery device 20 can include any one or combination of known implantable electrostimulatory devices capable of delivering electrical energy to an intraluminal target site in a subject, including, for example, a minimally invasive intraluminal electrode, such as the one disclosed in U.S. Patent Pub. No. 2006/0058597 A1, the entire contents of which are hereby incorporated by reference.

As shown in FIG. 2, the expandable electrode 24 comprises oppositely disposed first and second end portions 26 and 28 and a main body portion 30 extending between the end portions. The structure of the expandable electrode 24 may be a mesh, a zigzag wire, a spiral wire, an expandable stent, or other similar configuration that allows the expandable electrode to be collapsed and expanded. The expandable electrode 24 can be comprised of a material having a high modulus of elasticity, including, for example, cobalt-nickel alloys (e.g., Elgiloy), titanium, nickel-titanium alloys (e.g., Nitinol), cobalt-chromium alloys (e.g., Stellite), nickel-cobalt-chromium-molybdenum alloys (e.g., MP35N), graphite, ceramic, stainless steel, and hardened plastics. The expandable electrode 24 may also be made of a radio-opaque material or include radio-opaque markers (not shown) to facilitate fluoroscopic visualization.

Figure 4:
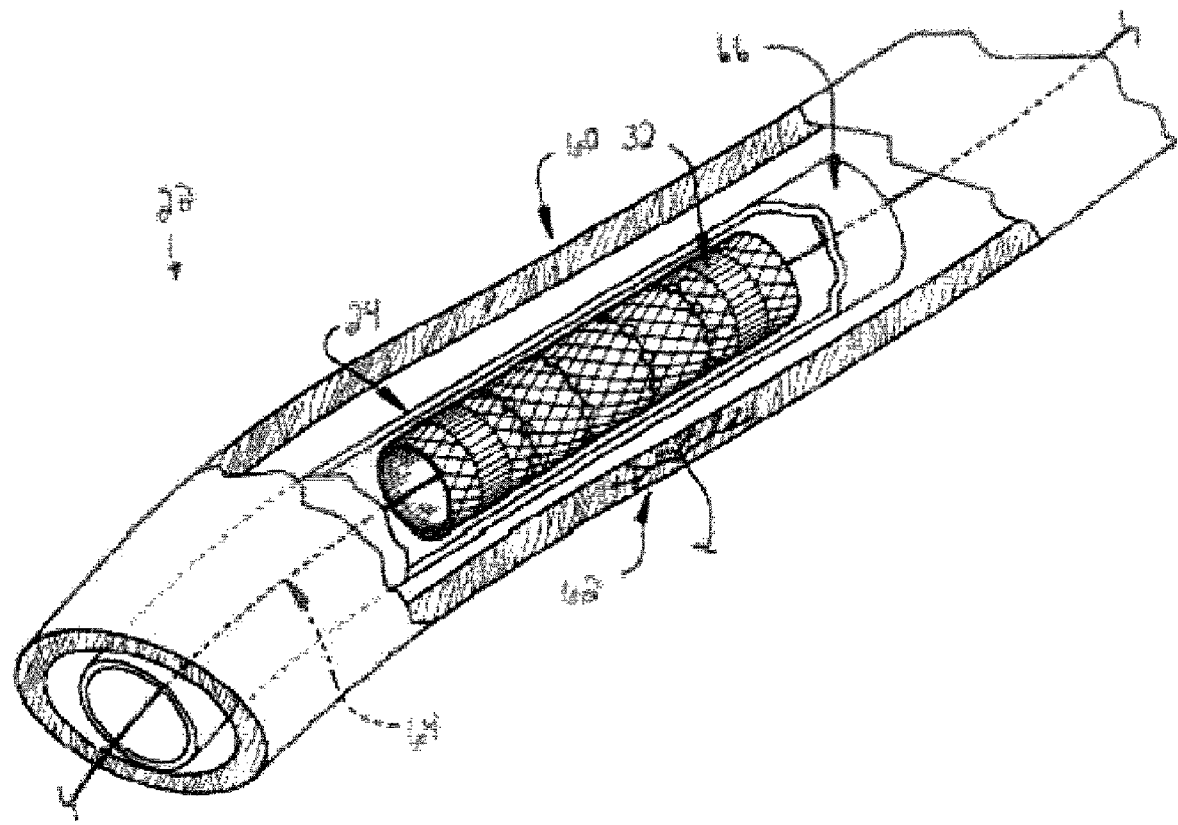
FIG. 4 is a cross-sectional view of the therapy delivery device in FIG. 1 in a collapsed configuration in the blood vessel.

At least one constraining band 32 (FIG. 4) may be placed around the circumference of the expandable electrode 24 to maintain the expandable electrode in a collapsed configuration. The constraining band 32 may comprise a suture, for example, and may be placed around the circumference of the expandable electrode 24 as needed. Removal of the constraining band 32 allows the expandable electrode 24 to self-expand and obtain an expanded configuration shown in FIG. 2. Where the constraining band 32 comprises a suture, for example, the suture may be manually broken or, alternatively, broken by the radial force generated when the expandable electrode 24 self-expands.

The expandable electrode 24 includes at least one electrode 34 for delivering electrical energy (e.g., an electric current) to an intraluminal target site. As shown in FIG. 2, the electrodes 34 have a flat, disc-like shape and are radially disposed about the circumference of the expandable electrode 24 in a multi-electrode array configuration. It will be appreciated, however, that the electrodes 34 may have any shape and size, including, for example, a triangular shape, a rectangular shape, an ovoid shape, and/or a band-like shape (e.g., a split band configuration), and are not limited to the shapes and sizes illustrated in FIG. 2. The electrodes 34 may be configured so that the expandable electrode 24 has a unipolar construction using the surround tissue as ground or, alternatively, a bipolar construction using leads connected to either end of the expandable electrode. The electrodes 34 may be made of any material capable of conducting electrical energy, such as platinum, platinum-iridium, or the like.

As shown in FIG. 2, the electrodes 34 can extend around only a portion or the entire circumference of the expandable electrode 24 in a radial fashion. Alternatively, the electrodes 34 may extend around only a portion or the entire circumference of the expandable electrode 24 in a sinusoidal or helical fashion (not shown). The entire length of the expandable electrode 24 may be covered with the electrodes 34 or, alternatively, only a portion of the expandable electrode, such as the first and second end portions 26 and 28, may be covered with the electrodes (not shown).

To facilitate focal modulation of the intraluminal target site, the electrodes 34 may wrap around the expandable electrode 24 any number of times to establish a desired electrode contact and coverage. Additionally or optionally, the entire surface area of the electrodes 34 may be conductive or, alternatively, only a portion of the surface area of the electrodes may be conductive. By modifying the conductivity of the surface of the electrodes 34, the surface area of the electrodes that contact the intraluminal target site may be selectively modified to facilitate focal delivery of electrical energy to nervous tissue of the ANS.

Figure 5:
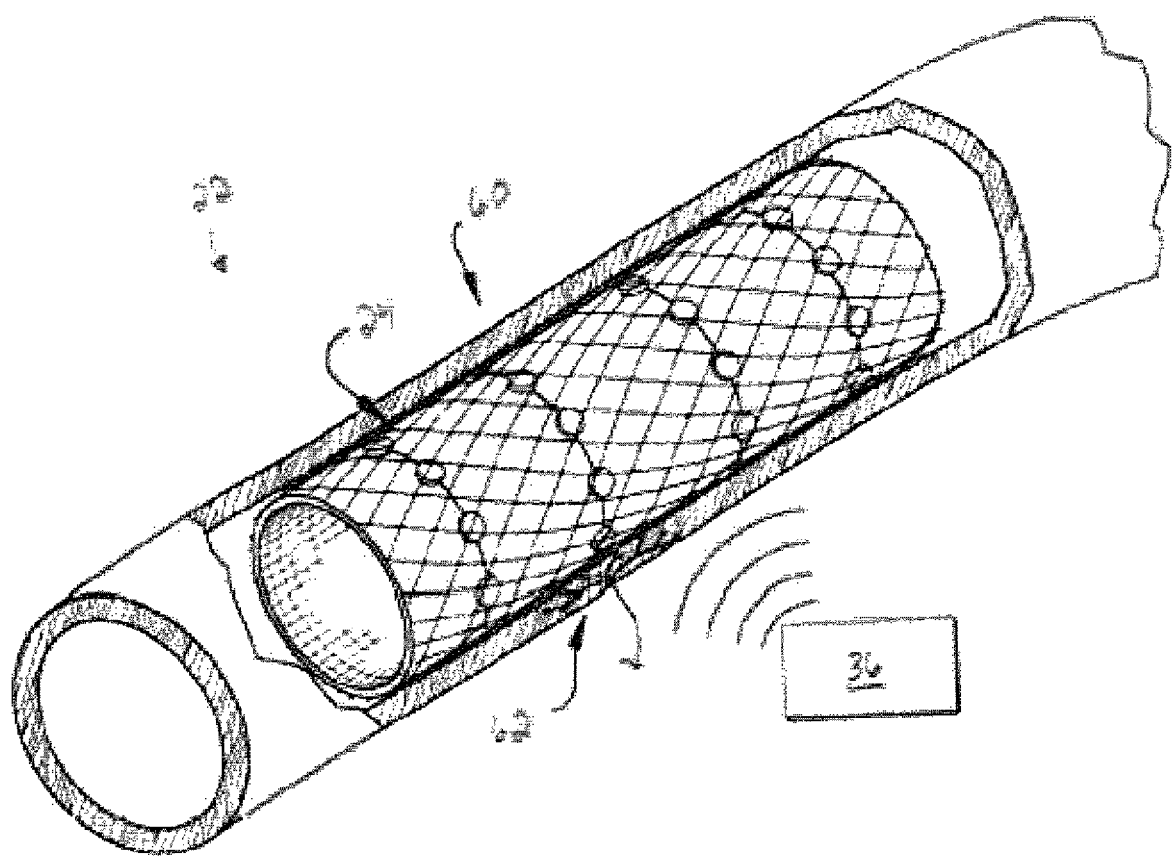
FIG. 5 is a cross-sectional view of the therapy delivery device in FIG. 1 in an expanded configuration in the blood vessel.

Electrical energy can be delivered to the electrodes 34 using a variety of internal, passive, or active energy delivery sources 36 (FIG. 5). The energy source 36 may include, for example, radio frequency (RF) energy, X-ray energy, microwave energy, acoustic or ultrasound energy such as focused ultrasound or high intensity focused ultrasound energy, light energy, electric field energy, magnetic field energy, combinations of the same, or the like. Alternatively, the energy source 36 may be provided through one or more biomechanical energy harvesting devices and/or mechanisms. The energy source 36 may be directly coupled to the expandable electrode 24 using an electrical lead (not shown). Alternatively, the energy source 36 may be wirelessly coupled to the expandable electrode 24 as shown in FIG. 5.

Electrical energy can be delivered to the electrodes 34 continuously, periodically, episodically, or a combination thereof. For example, electrical energy can be delivered in a unipolar, bipolar, and/or multipolar sequence or, alternatively, via a sequential wave, charge-balanced biphasic square wave, sine wave, or any combination thereof. Electrical energy can be delivered to all the electrodes 34 at once or, alternatively, to only a select number of desired electrodes. The particular voltage, current, and frequency delivered to the electrodes 34 may be varied as needed. For example, electrical energy can be delivered to the electrodes 34 at a constant voltage (e.g., at about 0.1 v to about 25 v), at a constant current (e.g., at about 25 microampes to about 50 milliamps), at a constant frequency (e.g., at about 5 Hz to about 10,000 Hz), and at a constant pulse-width (e.g., at about 50 μsec to about 10,000 μsec).

Referring again to FIG. 1, the expandable electrode 24 additionally comprises an insulative material 38 for isolating blood flow through a vessel 22 (FIG. 3) from the electrical energy. More particularly, the insulative material 38 (FIG. 2) serves as an electrical insulator, separating electrical energy from blood flow and facilitating delivery of the electrical energy to the intraluminal target site. The insulative material 38 is disposed radially inward of the electrodes 34 and extends along the entire length of the expandable electrode 24. Alternatively, the insulative material 38 may be attached to select portions of the expandable electrode 24, such as only the second end portion 28 and part of the main body portion 30 (not shown). The insulative material 38 may be disposed between the electrodes 34 and the expandable electrode 24 (not shown) or, alternatively, disposed about the lumen of the expandable electrode (not shown). The insulative material 38 generally has a low electrical conductivity and a non-thrombogenic surface. Examples of materials used to make the insulative material 38 are known in the art.

Figure 6A:
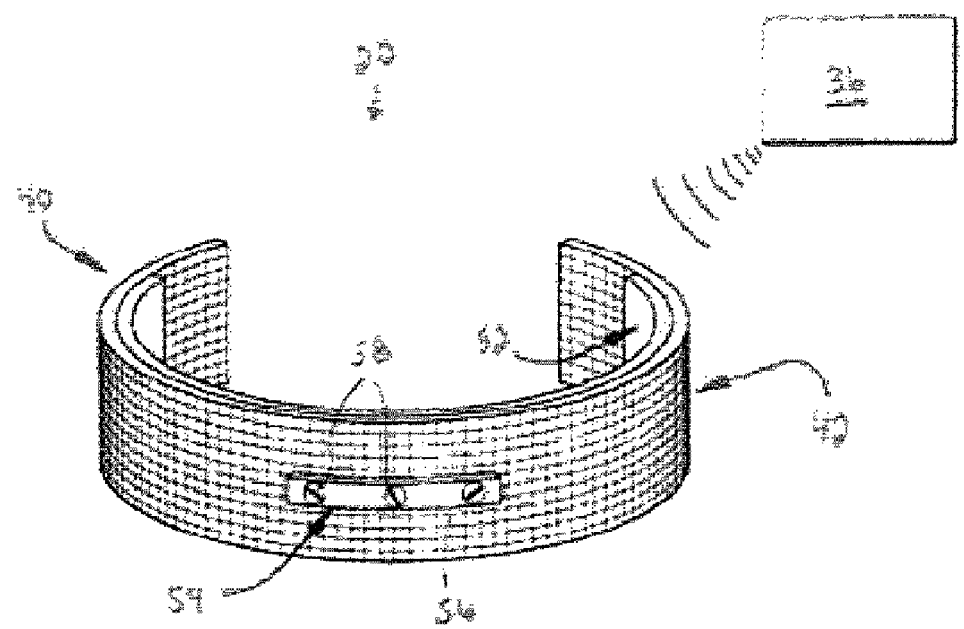
FIG. 6A is a perspective view showing an alternative embodiment of the therapy delivery device in FIG. 1.
Figure 6B:
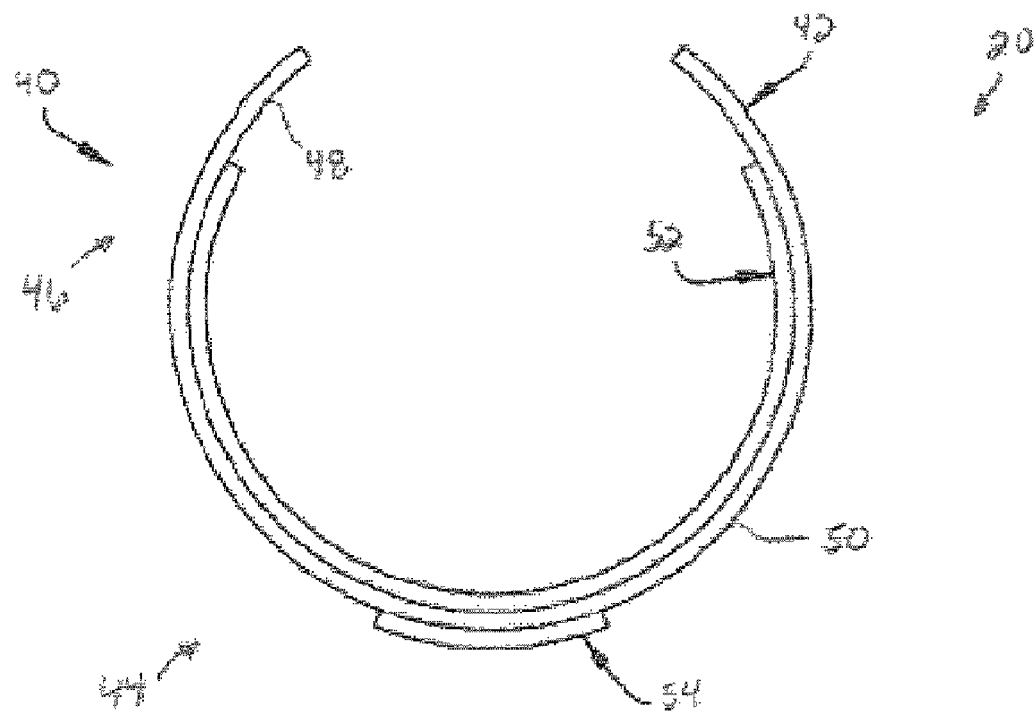
FIG. 6B is a top plan view of the therapy delivery device shown in FIG. 6A.

The therapy delivery device 20 can alternatively be constructed as shown in FIGS. 6A and 6B. In FIGS. 6A and 6B, the therapy delivery device 20 can comprise an implantable electrode assembly 40 having an elastomeric member 42 with first and second end portions 44 and 46 and oppositely disposed first and second surfaces 48 and 50. As described in further detail below, the particular geometry and flexible properties of the elastomeric member 42 allow the electrode assembly 40 to be securely positioned at an extra-luminal or intra-luminal target site.

The elastomeric member 42 may be comprised of a flexible, biocompatible material such as a polypropylene mesh, for example. Other examples of suitable materials include DACRON (Invista, Wichita, Kans.), GORETEX (W. L. Gore & Associates, Flagstaff, Ariz.), woven velour, polyurethane, or heparin-coated fabric. The elastomeric member 42 may have a C-shaped geometry as shown in FIGS. 6A and 6B, for example, or any other suitable geometry, such as a U- or V-shaped geometry. Alternatively, the elastomeric member 42 may comprise a complete ring or O-shaped configuration. It will be appreciated that the elastomeric member 42 may have any dimension (e.g., width, length, circumference, etc.) as required by a particular application of the electrode assembly 40.

The electrode assembly 40 can include at least one electrode 52 for delivering electrical energy to the intraluminal target site. The electrode 52 can be operably connected to at least a portion of the first surface 48 of the elastomeric member 42 and, as shown in FIGS. 6A and 6B, has a thin, flattened configuration. It will be appreciated, however, that the electrode 52 may have any shape and size, including, for example, a triangular shape, a rectangular shape, an ovoid shape, and/or a band-like shape (e.g., a split band configuration), and is not limited to the shape and size illustrated in FIGS. 6A and 6B. It will also be appreciated that the electrode 52 can comprise a ½ or ¼ ring configuration, a plate electrode, a paddle electrode, a cuff electrode, a cylindrical electrode, or the like.

The electrode 52 may be configured so that the electrode assembly 40 has a unipolar construction using the surround tissue as ground or, alternatively, a bipolar construction using leads connected to a portion of the electrode assembly. The electrode 52 may be made of any material capable of conducting an electrical current, such as titanium, platinum, platinum-iridium, or the like.

As shown in FIGS. 6A and 6B, the electrode 52 can extend around only a portion of the first surface 48 of the elastomeric member 42. It will be appreciated, however, that any portion of the first surface 48 may be covered by the electrode 52 including, for example, the entire first surface. To facilitate focal delivery of electrical energy to the intraluminal target site, the size and shape of the electrode 52 may be varied as needed. Additionally or optionally, the entire surface area of the electrode 52 may be conductive or, alternatively, only a portion of the surface area of the electrode may be conductive. By modifying the size, shape, and conductivity of the surface of the electrode 52, the surface area of the electrode that contacts the intraluminal target site may be selectively modified to facilitate focal delivery of electrical energy.

Electrical energy can be delivered to the electrode 52 using a variety of internal, passive, or active energy delivery sources 36. The energy source 36 may include, for example, RF energy, X-ray energy, microwave energy, acoustic or ultrasound energy such as focused ultrasound or high intensity focused ultrasound energy, light energy, electric field energy, magnetic field energy, combinations of the same, or the like. Alternatively, the energy source 36 may be provided through one or more biomechanical energy harvesting devices and/or mechanisms. As shown in FIG. 6A, for example, an RF energy source 36 may be wirelessly coupled to the electrode assembly 40. Alternatively, the energy source 36 may be directly coupled to the electrode assembly 40 using an electrical lead (not shown).

Electrical energy can be delivered to the electrode 52 continuously, periodically, episodically, or a combination thereof. For example, electrical energy can be delivered in a unipolar, bipolar, and/or multipolar sequence or, alternatively, via a sequential wave, charge-balanced biphasic square wave, sine wave, or any combination thereof. Where a plurality of electrodes 52 are disposed about the implantable electrode assembly 40, electrical energy can be delivered to all the electrodes at once or, alternatively, to only a select number of desired electrodes. The particular voltage, current, and frequency delivered to the electrode 52 may be varied as needed. For example, electrical energy can be delivered to the electrode 52 at a constant voltage (e.g., at about 0.1 v to about 25 v), at a constant current (e.g., at about 25 microampes to about 50 milliamps), at a constant frequency (e.g., at about 5 Hz to about 10,000 Hz), and at a constant pulse-width (e.g., at about 50 μsec to about 10,000 μsec).

It should be appreciated, however, that means other than, or in addition to, electrical energy, such as chemical or biological means, may also be delivered to the intraluminal target site and thereby effect a change in the ANS. For example, the electrode assembly 40 may include at least one therapeutic agent for eluting into the vascular tissue and/or blood stream. The therapeutic agent may be capable of preventing a variety of pathological conditions including, but not limited to, thrombosis, stenosis and inflammation. Accordingly, the therapeutic agent may include at least one of an anticoagulant, an antioxidant, a fibrinolytic, a steroid, an anti-apoptotic agent, and/or an anti-inflammatory agent.

Optionally or additionally, the therapeutic agent may be capable of treating or preventing other diseases or disease processes, such as microbial infections, for example. In these instances, the therapeutic agent may include an anti-microbial agent and/or a biological agent such as a cell, peptide, or nucleic acid. The therapeutic agent can be simply linked to a surface of the electrode assembly 40, embedded and released from within polymer materials, such as a polymer matrix, or surrounded by and released through a carrier.

Referring again to FIGS. 6A and 6B, the electrode 52 can be operably secured to the first surface 48 of the elastomeric member 42 by an attachment mechanism 54. The attachment mechanism 54 can comprise a metal member 56 operably coupled to the second surface 50 of the elastomeric member 42. As shown in FIG. 6A, the metal member 56 has a plurality of securing members 58 extending radially therethrough. The securing members 58 can extend through the elastomeric member 42 and secure the electrode 52 on the first surface 48 of the elastomeric member. It will be appreciated that the attachment mechanism 54 may include a variety of other devices and mechanisms for securing the electrode 52 to the elastomeric member 42. For example, screws, clips, pins, adhesives, and/or staples may be used. Alternatively, a magnetic mechanism (not shown) may also be used to secure the electrode 52 to the elastomeric member 42.

The electrode assembly 40 may also include a layer of biocompatible material (not shown) to facilitate bio compatibility of the electrode assembly. The layer of biocompatible material may be synthetic such as DACRON, GORETEX, woven velour, polyurethane, or heparin-coated fabric. Alternatively, the layer of biocompatible material may be a biological material such as bovine or equine pericardium, peritoneal tissue, an allograft, a homograft, patient graft, or a cell-seeded tissue. The biocompatible layer can cover the entire electrode assembly 40 or, alternatively, may be attached in pieces or interrupted sections to facilitate placement, of the electrode assembly.

The therapy delivery device 20 can alternatively include an electrode (not shown) capable of being implanted at an intravascular or intraluminal location and delivering electrical energy to an intraluminal target site. A variety of implantable electrodes capable of delivering electrical energy to an intravascular or intraluminal target site are known in the art and include, for example, those disclosed in U.S. Pat. No. 7,231, 260, PCT Publication No. WO2007/092330, and U.S. Patent Pub. Nos. 2007/0265687 A1, 2006/0142801 A1, and 2005/0240241 A1, the entire contents of which are hereby incorporated by reference.

Where the therapy delivery device 20 comprises an implantable electrode, the electrode may include other components needed for operation, such as a controller or programmer (not shown) and one or more connectors (not shown) for connecting the electrode to the controller. It will be appreciated that more than one electrode may be employed in the present invention. Additionally, it will be appreciated that the electrode may be the same or different than a second electrode in one or more aspects (e.g., shape, size, etc). The description of a representative electrode suitable for use in the present invention is applicable to other electrodes that may also be employed.

The electrode can be controllable to provide output signals that may be varied in voltage, frequency, pulse width, current and intensity. The electrode can provide both positive and negative current flow from the electrode, can be capable of stopping current flow from the electrode, and/or can change the direction of current flow from the electrode. For example, the electrode can have the capacity for variable output, linear output, and short pulse width.

The energy source (not shown) for the electrical energy can be provided by a battery or generator, such as a pulse generator operatively connected to the electrode. The energy source may be positioned in any suitable location, such as adjacent to the electrode (e.g., implanted adjacent the electrode), at a remote site in or on the subject's body, and/or away from the subject's body in a remote location. The electrode may be connected to the remotely positioned energy source using wires, for example. One type of energy source can include implantable generators, which may be analogous to cardiac pacemakers.

The electrode may be mono-polar, bipolar or multi-polar. In order to minimize the risk of an immune response against the electrode and to minimize damage to the electrode (e.g., corrosion from biological fluids), the electrode (and any wires and optional housing materials) can be made of inert materials, such as silicon, metal, plastic, and the like.

The therapy delivery device 20 can be part of an open- or closed-loop system. In an open-loop system, for example, a physician or subject may, at any time, manually or by the use of pumps, motorized elements, etc. adjust treatment parameters such as pulse amplitude, pulse width, pulse frequency, or duty cycle. Alternatively, in a closed-loop system, electrical parameters may be automatically adjusted in response to a sensed symptom or a related symptom indicative of the extent of the pulmonary disorder being treated. In a closed-loop feedback system, a sensor (not shown) that senses a condition of the body can be utilized. More detailed descriptions of sensors that may be employed in a closed-loop system, as well as other examples of sensors and feedback control techniques that may be employed are disclosed in U.S. Pat. No. 5,716,377, which is hereby incorporated by reference in its entirety.

Although described in more detail below, it should be appreciated that incorporating the therapy delivery device 20 as part of a closed-loop system can include placing a therapy delivery device in a vessel 22 substantially adjacent the intraluminal target site, detecting a bodily activity associated with a pulmonary disorder, and then activating the therapy delivery device to apply a therapy signal to the intraluminal target site in response to the detected bodily activity. Such bodily activity can include any characteristic or function of the body, such as respiratory function, body temperature regulation, blood pressure, metabolic activity, cerebral blood flow, pH levels, vital signs, galvanic skin responses, perspiration, electrocardiogram, electroencephalogram, action potential conduction, chemical production, body movement, response to external stimulation, speech, balance, motor activity, ocular activity, cognitive function, and the like.

The analysis of constituents of breath, for example, provides an easily accessible, non-invasive method of monitoring inflammation as a number of by-products of airway inflammation and oxidative stress are found in exhaled air. Accordingly, a closed-loop system can include a sensor for detecting at least one metabolic parameter associated with pulmonary inflammation from the exhaled vapor of a subject. Examples of the metabolic parameter can include, but are not limited to, eicosanoids (e.g., 8-isoprostanes, leukotriene$_4$ (LTE$_4$), LTC$_4$, LTD$_4$, LTB$_4$, PG, TX), NO-related products (e.g., nitrotyrosine, NO$_2^-$/NO$_3^-$, S-nitrosothiols), hydrogen peroxide, lipid peroxidation products, vasoactive amines, ammonia, cytokines (e.g., IL-1β, IL-2, IL-6, TNF-α, IL-8), and electrolytes (e.g., Na, Cl, Mg, Ca).

As noted above, one step of the method 10 includes inserting the therapy delivery device 20 into a vessel 22 of a subject at 12. The vessel 22 can include any artery or vein. Non-limiting examples of arteries into which the therapy delivery device 20 can be inserted include the aorta, including the ascending, descending, thoracic, abdominal and arch segments; carotid arteries; femoral arteries; brachial arteries; radial arteries; popliteal arteries; ulnar arteries; dorsalis pedias arteries; intercostals arteries; vertebral arteries; subclavian arteries; iliac arteries; renal arteries; pulmonary arteries; and tributaries thereof. Non-limiting examples of types of veins into which the therapy delivery device 20 can be inserted include jugular veins (external and internal); antebrachial veins; subclavian veins; axillary veins; iliac veins; sinuses; saphenous veins; intercostals veins; radial veins; brachial veins; femoral veins; renal veins; superior vena cava; inferior vena cava; pulmonary veins; and tributaries thereof.

Depending upon the clinical needs of the subject, the therapy delivery device 20 can be surgically inserted into the vessel 22 via a percutaneous, transvascular, laparoscopic, or open surgical procedure. It should be appreciated that the therapy delivery device 20 can also be inserted into an intraluminal space, such as the trachea, bronchus, bronchioles, esophagus, stomach, large intestine, small intestine, oral cavity, and/or nasal cavity.

After inserting the therapy delivery device 20 into a vessel 22 of the subject, the therapy delivery device can be advanced to a point substantially adjacent an intraluminal target site of the ANS at 14. The intraluminal target site includes an intravascular or intraluminal location at which the therapy delivery device 20 can be positioned. The intraluminal target site can comprise nervous tissue associated with the ANS. For example, the intraluminal target site can include a portion of a vessel wall that is innervated by (or in electrical communication with) a nerve, neuron, and/or nervous tissue of the ANS. Examples of suitable intraluminal target sites include, without limitation, vascular or luminal sites innervated by and/or in electrical communication with neurons, axons, fibers, tracts, nerves, plexus, afferent plexus fibers, efferent plexus fibers, ganglion, pre-ganglionic fibers, post-ganglionic fibers, cervical sympathetic ganglia/ganglion, thoracic sympathetic ganglia/ganglion, afferents, efferents, a spinal nerve, a postganglionic fiber of a spinal nerve, a sympathetic chain ganglion, a thoracic sympathetic chain ganglion, a cervical ganglion, a lower cervical ganglion, an inferior cervical ganglion, an intramural ganglion, a splanchnic nerve, an esophageal plexus, a cardiac plexus, a pulmonary plexus, an anterior pulmonary plexus, a posterior pulmonary plexus, a celiac plexus, a hypogastric plexus, an inferior mesenteric ganglion, a celiac ganglion, and a superior mesenteric ganglion.

At 16, the therapy delivery device 20 is activated to deliver a therapy signal to the intraluminal target site and thereby treat the pulmonary disorder. The therapy signal includes an electric signal capable of electrically modulating the nervous tissue of the ANS. By "electrically modulating," it is meant that at least a portion of the ANS is altered or changed by electrical means. Electrical modulation of the ANS may affect central motor output, nerve conduction, neurotransmitter release, synaptic transmission, and/or receptor activation. For example, at least a portion of the ANS may be electrically modulated to alter, shift, or change parasympathetic function from a first state to a second state, where the second state is characterized by an increase or decrease in parasympathetic function relative to the first state. Alternatively, at least a portion of the ANS may be electrically modulated to alter, shift, or change sympathetic function from a first state to a second state, where the second state is characterized by an increase or decrease in sympathetic function relative to the first state.

It will be appreciated that delivering electrical energy to the intraluminal target site can modulate the ANS in any desirable combination of ways, including, for example, increasing both parasympathetic and sympathetic function, increasing parasympathetic function while decreasing sympathetic function, decreasing both parasympathetic and sympathetic function, and decreasing parasympathetic function while increasing sympathetic function.

As the method 10 of the present invention generally includes electrical modulation of at least a portion of the ANS, it will be appreciated that the electrical modulation of the ANS may be systemic or regional (i.e., local). In other words, the entire PNS and/or SNS may be electrically modulated. Alternatively, only a portion of the PNS and/or SNS may be electrically modulated. As will be described in greater detail below, any part of the present invention may be performed manually or automatically.

Figure 3:
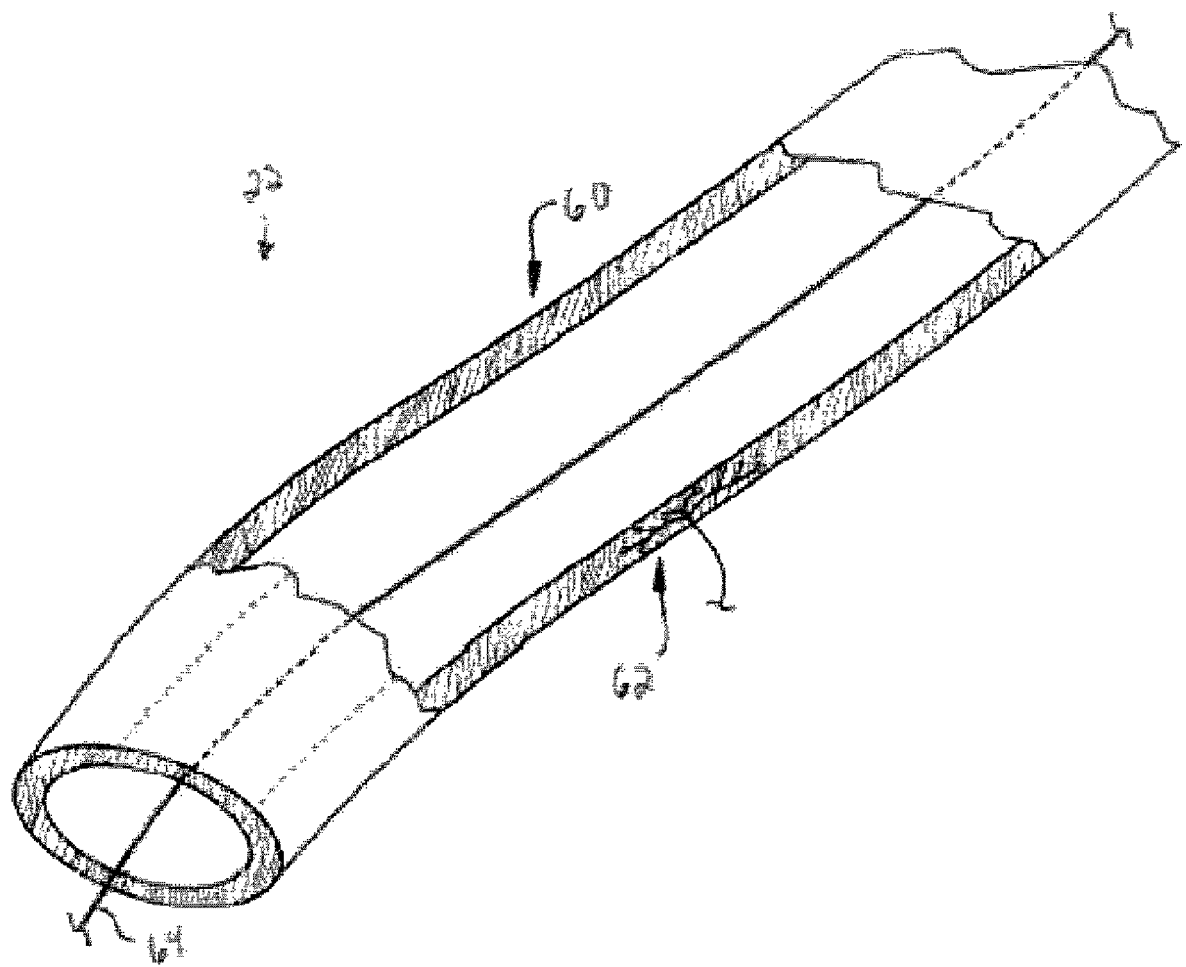
FIG. 3 is a cross-sectional view of a guidewire disposed in a blood vessel.

In an example of the method 10, a human subject having asthma can be treated using the therapy delivery device 20 shown in FIG. 2. According to the method 10, the expandable electrode 24 of FIG. 2 is implanted using a minimally invasive, percutaneous, or endovascular approach. It should be appreciated, however, that a minimally invasive surgical approach may also be used. The expandable electrode 24, or only thereof, is positioned substantially adjacent an intraluminal target site in a blood vessel 22. For purposes of illustration only, the present invention is described with reference to the expandable electrode 24 being positioned in a portion of the left pulmonary artery 60 (FIG. 3). As described in more detail below, the left pulmonary artery 60 may be an intraluminal target site because a portion of the anterior pulmonary plexus 62 (FIGS. 3 and 7A-C) crosses a portion of the left pulmonary artery.

Prior to use of the expandable electrode 24, the dimensions of the left pulmonary artery 60 will need to be determined. Various methods and devices for determining the dimensions of the left pulmonary artery 60 are known in the art, including, for example, computed tomography, magnetic resonance imaging, angiography and fluoroscopy. After determining the dimensions of the left pulmonary artery 60, an appropriately-sized expandable electrode 24 is chosen. The expandable electrode 24 is suitably sized, for example, so that the dimensions of the expandable electrode in the expanded configuration correspond to the dimensions of the left pulmonary artery 60.

Percutaneous placement of the expandable electrode 24 starts by accessing a bodily vessel with a delivery device 64 (FIG. 3). For instance, a guidewire 64 may be introduced into the vasculature of the subject via a vascular opening (not shown). Vascular access may be through a peripheral venous access site (not shown), such as a femoral vein (not shown). The guidewire 64 is inserted through the incision into the inferior vena cava (not shown) and then urged into the right atrium (not shown), across the tricuspid valve (not shown) into the right ventricle (not shown), and then through the pulmonary valve (not shown) into the left pulmonary artery 60.

Next, the expandable electrode 24 is placed in a delivery catheter 66 (FIG. 4) in a collapsed configuration and securely attached to a proximal end (not shown) of the guidewire 64. The delivery catheter 66 is then advanced over the guidewire 64 until the delivery catheter is appropriately positioned in the left pulmonary artery 60. Once the expandable electrode 24 is appropriately positioned in the left pulmonary artery 60, the delivery catheter 66 is removed and the constraining bands 32 are progressively released (i.e., broken) by the radial force generated by the self-expanding expandable electrode. When all of the constraining bands 32 have been released, the expandable electrode 24 obtains the expanded configuration and the expandable electrode is securely positioned in the left pulmonary artery 60 (FIG. 5). With the expandable electrode 24 securely positioned in the left pulmonary artery 60, the guidewire 64 may then be removed from the vasculature of the subject.

After the guidewire 64 has been removed from the subject, electrical energy is delivered to the expandable electrode 24. As shown in FIG. 5, RF energy is delivered to the expandable electrode 24 via a wirelessly coupled energy delivery source 36. As electrical energy is delivered to the expandable electrode 24, the electrodes 34 conduct electrical energy to the vascular wall of the left pulmonary artery 60. The electrical energy then modulates at least a portion of the anterior pulmonary plexus 62. For example, electrical stimulation of the anterior pulmonary plexus 62 increases sympathetic nerve function, in turn causing the bronchioles to dilate and thus treat the asthmatic symptoms of the subject.

Figure 7A:
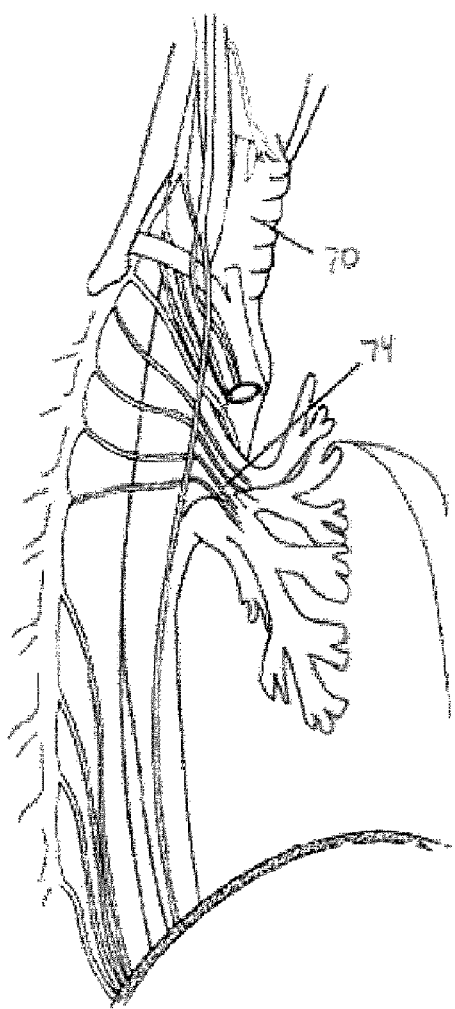
FIG. 7A is a schematic illustration showing the major nerves contributing to the pulmonary plexus.
Figure 7B:
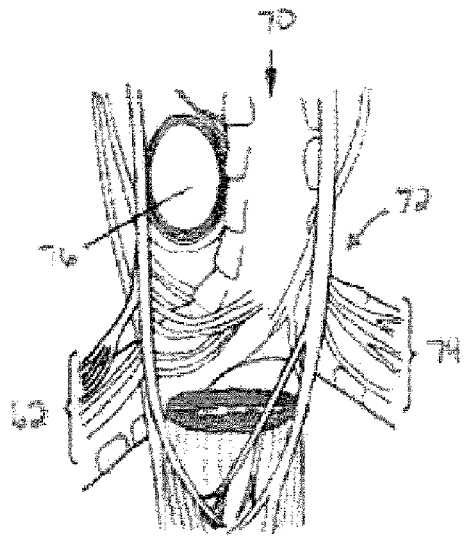
FIG. 7B is a magnified schematic illustration showing a posterior view of the pulmonary plexus.
Figure 7C:
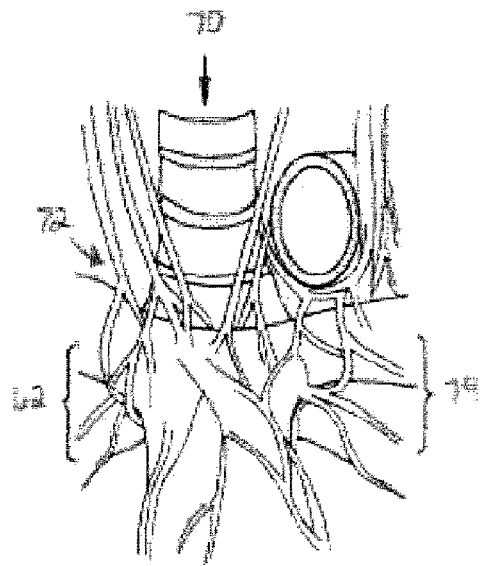
FIG. 7C is a magnified schematic illustration showing an anterior view of the pulmonary plexus.
Figure 8A:
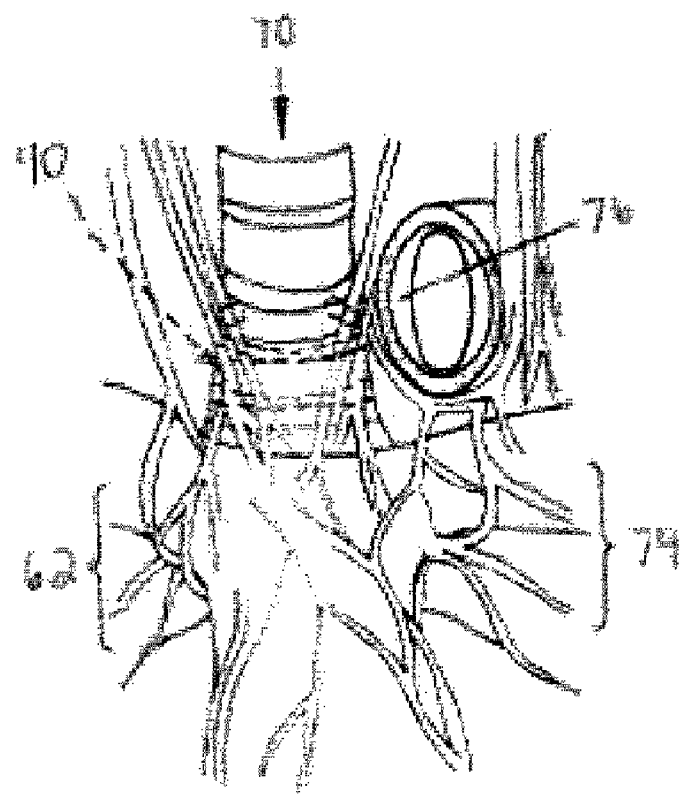
FIG. 8A is a schematic illustration showing the therapy delivery device of FIG. 6A implanted in the trachea.
Figure 8B:
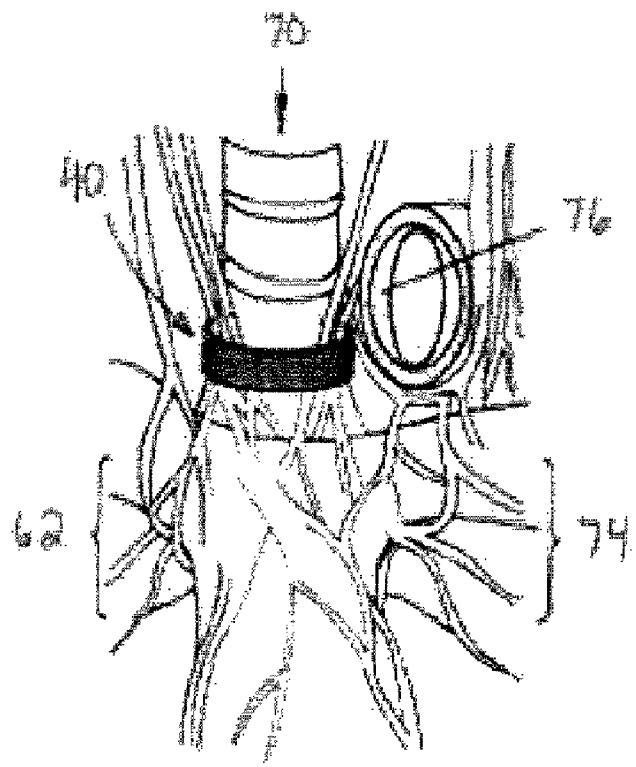
FIG. 8B is a schematic illustration showing the therapy delivery device of FIG. 6A secured about an extra-luminal aspect of the trachea.

In another example of the method 10, a therapy delivery device 20, such as the one shown in FIGS. 6A and 6B, can be used to treat asthma in a human subject. The electrode assembly 40 of FIGS. 6A and 6B may be implanted at or substantially adjacent an intraluminal target site comprising the pulmonary plexus 68 (FIGS. 7A-C). Various surgical and/or percutaneous approaches may be used to access an intraluminal target site at the pulmonary plexus 68. Examples of suitable approaches include, but are not limited to, trans-tracheal, trans-mediastinal, transvenous (e.g., through the pulmonary trunk), trans-aortic, and trans-esophageal routes.

Where a trans-tracheal approach is used, an endoscopic device (not shown), such as a laryngoscope may be used to place the electrode assembly 40. The electrode assembly 40 can be attached to the laryngoscope, for example, and then advanced into the subject's trachea 70 (FIGS. 7A-C) until the electrode assembly is positioned at or near the carina 72. Once the electrode assembly 40 is properly positioned, the electrode assembly can be released from the laryngoscope so that the elastomeric member 42 expands against the wall of the trachea 70 and is securely positioned substantially adjacent the pulmonary plexus 68 (FIG. 8A).

Depending upon the orientation of the electrode assembly 40, the SNS or PNS can be electrically modulated. For example, if delivery of electrical energy is made posteriorily, then the parasympathetic innervation can be selectively modulated. Alternatively, if delivery of electrical energy is made anteriorily, then sympathetic innervation can be selectively modulated. The electrode assembly 40 can thus modulate different parts of pulmonary plexus 68 depending on the location of the electrode assembly. Electrode assemblies 40 placed in the pulmonary trunk (not shown in detail) or the aorta 76 (not shown in detail) can also selectively modulate the anterior pulmonary plexus 62. Additionally, electrode assemblies 40 placed at the esophagus (e.g., the esophageal plexus) (not shown) can selectively modulate the posterior pulmonary plexus 74.

During delivery of electrical energy to the electrode assembly 40, at least one metabolic parameter of interest (described above) may be monitored by, for example, a respiratory monitor (not shown) (or similar device) or, alternatively, via a sensor (not shown). The sensor may comprise any suitable device that measures or monitors a parameter indicative of the need to modify the activity of the electrode assembly 40. For example, the sensor may comprise a physiologic transducer or gauge.

Where the sensor is positioned at a local location, such as at an intra- or extra-luminal location on the tracheo-bronchial tree (not shown in detail), for example, the sensor may measure one or more physiological parameters including, but not limited to, $pO_2$, $pCO_2$, histamine, capsaicin, substance P, bradykinin, thromboxane, $LTC_4$, methacholine, neurokinin A, 5-HT, ATP, adenosine, changes in luminal pressure (e.g., exceeding about 10 to about +10 cm $H_2O$), brochopsasms, contraction of the tracheal smooth muscles, mucin output, contraction of the tracheal smooth muscles, and vasodilatation.

Alternatively, where the sensor is positioned at a remote location, such as at an intravascular location, the sensor may measure one or more physiological parameters including, but not limited to, interleukins, bradykinin, tachykinin, blood pressure (systolic, diastolic, average or pulse pressure), blood volumetric flow rate, blood flow velocity, blood pH, $O_2$ or $CO_2$ content, nitrogen content, blood glucose, inflammatory mediators, tissue factors, mixed venous oxygen saturation ($SVO_2$), vasoactivity, nerve activity, and tissue activity or composition.

An electrical energy delivery regimen comprising a desired temporal and spatial distribution of electrical energy to the intraluminal target site of the subject may be selected to promote long term efficacy of the present invention. It is contemplated that uninterrupted or otherwise unchanging electrical modulation of the intraluminal target site may result in the nervous tissue present at the intraluminal target site to become less responsive over time, thereby diminishing the long term effectiveness of the therapy. Therefore, the electrical energy delivery regimen maybe selected to activate, deactivate or otherwise modulate the electrode assembly 40 in such a way that therapeutic efficacy is maintained for a desired period of time.

In addition to maintaining therapeutic efficacy over time, the electrical energy delivery regimen-maybe selected to reduce the power requirement/consumption of the electrode assembly 40. For example, the electrical energy delivery regimen may dictate that the electrode assembly 40 be initially activated at a relatively higher energy and/or power level, and then subsequently activated at a relatively lower energy and/or power level. The first level attains the desired initial therapeutic effect, and the second (lower) level sustains the desired therapeutic effect long term. By reducing the energy and/or power levels after the desired therapeutic effect is initially attained, the energy required or consumed by the electrode assembly 40 is also reduced long term.

Unwanted collateral stimulation of nervous tissue may be limited by creating localized cells or electrical fields (i.e., by limiting the electrical field beyond the intraluminal target site). Localized cells may be created by, for example, spacing one or more electrodes 52 very close together or biasing the electrical field with conductors and/or magnetic fields. For example, electrical fields may be localized or shaped by using electrodes 52 with different geometries, by using one or more multiple electrodes, and/or by modifying the frequency, pulse-width, voltage, stimulation waveforms, paired pulses, sequential pulses, and/or combinations thereof.

It should be appreciated that the electrode assembly 40 can be placed in direct contact with the pulmonary plexus 68 using a trans-mediastinal approach, for example. Where a trans-mediastinal approach is used, an anterior mediastinoscopy or thoracoscopy may be used to place the electrode assembly 40. The advantage of thoracoscopy is the visibility, even to the subcarinal anterior mediastinum (not shown). The mediastinoscopy can be performed under general anesthesia using standard KARL STORZ mediastinoscope (Culver City, Calif.) (not shown) either with or without video assistance.

An incision (not shown) can be made in the suprasternal notch (not shown) and dissection performed caudally to the thyroid isthmus (not shown) and continued by blunt dissection into the pretracheal space. Once the carina 72 is identified, the electrode assembly 40 can be placed around the distal-most part of trachea 70 above the surrounding soft tissue so that the elastomeric member 42 surrounds the anterior pulmonary plexus 62, for example. Electric current can then be delivered to the electrode assembly 40 (as described above) to modulate sympathetic function and thereby treat asthmatic symptoms.

In another example of the present invention, a trans-esophageal approach can be used to treat a pulmonary disorder. In one step of the method, a therapy delivery device 20 can be inserted or implanted into the esophagus of a subject so that the therapy delivery device is substantially adjacent a portion of the ANS. Once the therapy delivery device 20 is appropriately positioned, electrical energy can be delivered to the therapy delivery device so that electrical energy passes through the esophageal wall and modulates the ANS to treat the pulmonary disorder. To treat a subject having asthma, for example, the therapy delivery device 20 can be inserted or implanted in the subject's esophagus so that the therapy delivery device is substantially adjacent the anterior pulmonary plexus 62. Once the therapy delivery device 20 is appropriately positioned in the esophagus, electrical energy (e.g., RF energy) can be delivered to the therapy delivery device. The therapy delivery device 20 can then conduct electrical energy through the esophageal wall and into at least a portion of the anterior pulmonary plexus 62. Electrical stimulation of the anterior pulmonary plexus 62 can increase sympathetic nerve function, in turn causing the bronchioles to dilate and thus treat the asthmatic symptoms of the subject. It will be appreciated that the therapy delivery device 20 can be inserted or implanted into the esophagus only shortly (i.e., acutely) or, alternatively, implanted for long term (i.e., chronic) therapy.

Figure 9:
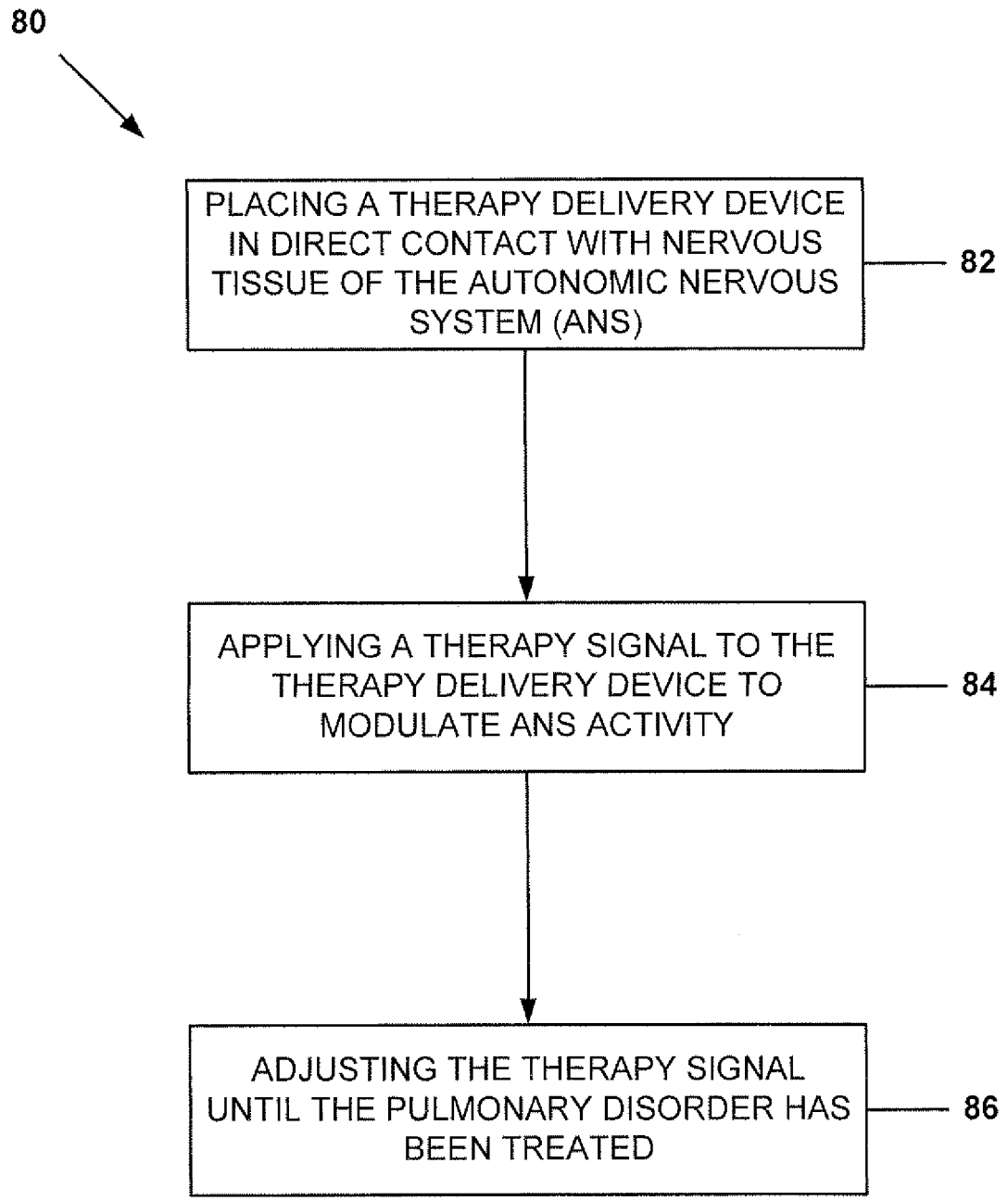
FIG. 9 is a flow diagram illustrating an alternative embodiment of the present invention.

Another embodiment of the present invention is illustrated in FIG. 9. In FIG. 9, a method 80 for treating a pulmonary disorder can include placing a therapy delivery device in direct contact with nervous tissue of the ANS at 82. By "direct" it is meant that a therapy delivery device 20 is placed on or near nervous tissue capable of effecting a change in the ANS of a subject. Therapy delivery devices 20 that can be directly contacted with nervous tissue of the ANS are known in the art and can include, for example, plate electrodes, paddle electrodes, cuff electrodes, cylindrical electrodes, and the like. Further examples of therapy delivery devices 20 that can be directly contacted with nervous tissue of the ANS can include, but are not limited to, those disclosed in: U.S. Pat. Nos. 7,277,757, 6,572,543, and 6,748,275; PCT Pub. No. WO93001862 A1; and U.S. Patent Pub. Nos. 2005/0137645 A1, 2007/0106339 A1, 2006/0293720 A1, 2007/0213782 A1, 2007/0021795 A1, 2006/0247729 A1, 2007/0027496 A1, 2007/0106339 A1, 2006/0224211 A1, 2004/0153127 A1, 2007/0173893 A1, 2006/0282131 A1, and 2006/0282127 A1, the entireties of which are hereby incorporated by reference.

As described above, the therapy delivery device 20 can be part of an open- or closed-loop system to directly modulate nervous tissue of the ANS. Examples of nervous tissue which can be directly modulated by the method 80 can include, but are not limited to, the sympathetic nerve chain, the vagus nerve, the phrenic nerve, the pulmonary plexus, the hypoglossal nerve, the glossopharyngeal nerve, the laryngeal nerve, and the vestibular nerve. Other examples of nervous tissue which can be directly modulated by the method 80 can include any one or combination of the nerves disclosed in U.S. Pat. No. 7,149,574 and U.S. Patent Pub. No. 2005/0065573 A1, the entireties of which are hereby incorporated by reference.

After placing the therapy delivery device 20 in direct contact with a nerve, a therapy signal can be applied to the therapy delivery device to electrically modulate ANS activity at 84. The therapy signal can include an electric signal which is directly delivered to the nerve tissue and which is capable of electrically modulating the tissue. Electrical modulation of the ANS may affect central motor output, nerve conduction, neurotransmitter release, synaptic transmission, and/or receptor activation. For example, at least a portion of the ANS may be electrically modulated to alter, shift, or change parasympathetic function from a first state to a second state, where the second state is characterized by an increase or decrease in parasympathetic function relative to the first state. Alternatively, at least a portion of the ANS may be electrically modulated to alter, shift, or change sympathetic function from a first state to a second state, where the second state is characterized by an increase or decrease in sympathetic function relative to the first state.

It will be appreciated that delivering electrical energy to the intraluminal target site can modulate the ANS in any desirable combination of ways, including, for example, increasing both parasympathetic and sympathetic function, increasing parasympathetic function while decreasing sympathetic function, decreasing both parasympathetic and sympathetic function, and decreasing parasympathetic function while increasing sympathetic function.

At 86, the therapy signal can be adjusted until the pulmonary disorder has been treated. Using an open-loop system, for example, a physician or subject may, at any time, manually or by the use of pumps motorized elements, etc. adjust treatment parameters such as pulse amplitude, pulse width, pulse frequency, or duty cycle. Alternatively, in a closed-loop system, the electrical parameters may be automatically adjusted in response to a sensed symptom, metabolic parameter, or a related symptom indicative of the extent of the pulmonary disorder being treated.

In an example of the method 80, a subject suffering from asthma may be treated by directly stimulating nervous tissue of the ANS with a therapy delivery device 20. More particularly, a therapy delivery device 20 comprising a pulse generator (not shown) may be used to apply an electrical impulse to a selected region of the vagus nerve (not shown), for example. The selected region can comprise, for example, at least one nerve fiber emanating from the tenth cranial nerve (the vagus nerve) and, in particular, at least one of the anterior bronchial branches thereof, or alternatively at least one of the posterior bronchial branches thereof. For example, the impulse may be provided to at least one of the anterior pulmonary or posterior pulmonary plexuses 62 and 74 aligned with the exterior of the lung (not shown). As necessary, the impulse may be directed to nerves innervating only the bronchial tree and lung tissue itself. In addition, the impulse may be directed to a region of the vagus nerve to block and/or modulate both the cardiac and bronchial branches.

The pulse generator can include an electrical impulse generator (not shown), a power source (not shown) coupled to the electrical impulse generator, a control unit (not shown) in communication with the electrical impulse generator and coupled to the power source, and electrodes (not shown) coupled to the electrical impulse generator for attachment via leads (not shown) to one or more selected regions of the vagus nerve. Methods for stimulating the SNS, as well as descriptions of pulse generators that may be used to do so, are described in U.S. Patent Pub. Nos. 2005/0075701 A1 and 2005/0075702 A1, the entireties of which are hereby incorporated by reference.

The pulse generator can be implanted using a known surgical approach (e.g., percutaneously or subcutaneously). Using a percutaneous approach, for example, the pulse generator can be implanted in the subject such that at least one electrode of the pulse generator is placed in direct contact with a selected region of the vagus nerve. For example, at least one electrode can be placed in direct contact with the anterior pulmonary plexus 62. It will be appreciated that additional electrodes may be placed at other selected regions of the vagus nerve.

After the pulse generator, and in particular the electrode, is securely positioned in direct contact with the anterior pulmonary plexus 62, a therapy signal can be delivered to the electrode to modulate the function or activity of at least a portion of the anterior pulmonary plexus. For example, an electrical signal may be sent from the control unit to the electrical impulse generator to relay an electrical impulse to the electrode. Delivery of the electrical impulse to the electrode causes electric current to be delivered from the electrode to the at least a portion of the anterior pulmonary plexus 62. The electric current, in turn, can modulate the at least one portion of the anterior pulmonary plexus 62 and thereby increase overall sympathetic function in the subject, for example. An increase in sympathetic function can cause the bronchioles to dilate and thus reduce or eliminate the asthmatic symptoms of the subject.

From the above description of the invention, those skilled in the art will perceive improvements, changes and modifications. Such improvements, changes and modifications are within the skill of the art and are intended to be covered by the appended claims.

Having described the invention, I claim:

1. A method for treating asthma in a subject, said method comprising the steps of:
    inserting a therapy delivery device into a subclavian artery or a subclavian vein of the subject;
    advancing the therapy delivery device to a point substantially adjacent an intraluminal target site of the autonomic nervous system (ANS); and
    activating the therapy delivery device to deliver a therapy signal to the intraluminal target site of the ANS to treat the asthma; and
    wherein the intraluminal target site is in electrical communication with nervous tissue selected from the group consisting of a spinal nerve, pre- or post-ganglionic autonomic fibers, a sympathetic chain ganglion, a thoracic sympathetic chain ganglion, a cervical ganglion, a superior cervical ganglion, a middle cervical ganglion, a lower cervical ganglion, an inferior cervical ganglion, an intramural ganglion, an esophageal plexus, a cardiac plexus, a pulmonary plexus, an anterior pulmonary plexus, and a posterior pulmonary plexus.

2. The method of claim 1 further comprising the steps of:
    sensing a bodily activity associated with the asthma;
    generating a sensor signal based on the bodily activity; and
    activating the therapy delivery device to adjust application of the therapy signal to the intraluminal target site in response to the sensor signal to treat the asthma.

3. The method of claim 1, said step of activating the therapy delivery device further including increasing the sympathetic activity of the nervous tissue.

4. A method for treating asthma in a subject, said method comprising the steps of:
    inserting a therapy delivery device into a renal artery or a renal vein of the subject;
    advancing the therapy delivery device to a point substantially adjacent an intraluminal target site of the ANS; and
    activating the therapy delivery device to deliver a therapy signal to the intraluminal target site of the ANS to treat the asthma;
    wherein the intraluminal target site is in electrical communication with nervous tissue selected from the group consisting of a spinal nerve, pre- or post-ganglionic autonomic fibers, a sympathetic chain ganglion, an intramural ganglion, a splanchnic nerve, an esophageal plexus, a celiac plexus, a hypogastric plexus, an inferior mesenteric ganglion, a celiac ganglion, and a superior mesenteric ganglion.

5. The method of claim 4 further comprising the steps of:
    sensing a bodily activity associated with the asthma;
    generating a sensor signal based on the bodily activity; and
    activating the therapy delivery device to adjust application of the therapy signal to the intraluminal target site in response to the sensor signal to treat the asthma.

6. A method for treating asthma in a subject, said method comprising the steps of:
    inserting a therapy delivery device into an intercostal vein or an intercostal artery of the subject;
    advancing the therapy delivery device to a point substantially adjacent an intraluminal target site of the ANS; and
    activating the therapy delivery device to deliver a therapy signal to the intraluminal target site of the ANS to treat the asthma;
    wherein the intraluminal target site is in electrical communication with nervous tissue selected from the group consisting of a spinal nerve, pre- or post-ganglionic autonomic fibers, a sympathetic chain ganglion, a thoracic sympathetic chain ganglion, an intramural ganglion, a splanchnic nerve, an esophageal plexus, a cardiac plexus, a pulmonary plexus, an anterior pulmonary plexus, a posterior pulmonary plexus and a celiac plexus.

7. A method for treating asthma in a subject, said method comprising the steps of:
    inserting a therapy delivery device into a jugular vein of the subject;
    advancing the therapy delivery device to a point substantially adjacent an intraluminal target site of the ANS; and
    activating the therapy delivery device to deliver a therapy signal to the intraluminal target site of the ANS to treat the asthma;
    wherein the intraluminal target site is in electrical communication with nervous tissue selected from the group consisting of a spinal nerve, pre- or post-ganglionic autonomic fibers, a sympathetic chain ganglion, a cervical ganglion, a superior cervical ganglion, a middle cervical ganglion, a lower cervical ganglion, an inferior cervical ganglion, and an intramural ganglion.

8. The method of claim 7, wherein the jugular vein is an internal jugular vein.

9. The method of claim 7, wherein the jugular vein is an external jugular vein.

10. A method for treating asthma in a subject, said method comprising the steps of:
    inserting a therapy delivery device into a carotid artery of the subject;
    advancing the therapy delivery device to a point substantially adjacent an intraluminal target site of the ANS; and activating the therapy delivery device to deliver a therapy signal to the intraluminal target site of the ANS to treat the asthma;

wherein the intraluminal target site is in electrical communication with nervous tissue selected from the group consisting of a spinal nerve, pre- or post-ganglionic autonomic fibers, a sympathetic chain ganglion, a cervical ganglion, a superior cervical ganglion, a middle cervical ganglion, a lower cervical ganglion, an inferior cervical ganglion, and an intramural ganglion.

11. The method of claim 10, wherein the carotid artery is an internal carotid artery.

12. The method of claim 10, wherein the carotid artery is an external carotid artery.

13. The method of claim 10, wherein the carotid artery is a common carotid artery.

* * * * *